United States Patent
Chen et al.

(10) Patent No.: US 11,712,363 B2
(45) Date of Patent: Aug. 1, 2023

(54) ADJUSTABLE ORAL INTERFACE FOR NEGATIVE-PRESSURE THERAPY SYSTEM

(71) Applicant: Somnics, Inc., Zhubei (TW)

(72) Inventors: Chung-Chu Chen, Zhubei (TW); Tung-Ming Yu, Zhubei (TW); Yin-Ruei Chen, Zhubei (TW)

(73) Assignee: Somnics, Inc., Zhubei (TW)

( * ) Notice: Subject to any disclaimer, the term of this patent is extended or adjusted under 35 U.S.C. 154(b) by 53 days.

(21) Appl. No.: 16/762,646

(22) PCT Filed: Nov. 27, 2018

(86) PCT No.: PCT/CN2018/117689
§ 371 (c)(1),
(2) Date: May 8, 2020

(87) PCT Pub. No.: WO2019/101213
PCT Pub. Date: May 31, 2019

(65) Prior Publication Data
US 2020/0352776 A1    Nov. 12, 2020

Related U.S. Application Data

(60) Provisional application No. 62/590,663, filed on Nov. 27, 2017.

(51) Int. Cl.
*A61F 5/56* (2006.01)
(52) U.S. Cl.
CPC ..................... *A61F 5/56* (2013.01)
(58) Field of Classification Search
CPC .......... A61F 5/56; A61F 5/566; A61F 2/2803; A61F 2002/30991; A61F 2005/563;
(Continued)

(56) References Cited

U.S. PATENT DOCUMENTS

| 2008/0216843 A1* | 9/2008 | Jiang | A61F 5/566 128/848 |
| 2009/0120446 A1* | 5/2009 | Vaska | A61F 5/566 128/846 |

(Continued)

FOREIGN PATENT DOCUMENTS

| CN | 102028574 A | 4/2011 |
| CN | 103140192 A | 6/2013 |

(Continued)

OTHER PUBLICATIONS

International Search Report (PCT/ISA/210) issued in PCT/CN2018/117689 dated Feb. 27, 2019.

*Primary Examiner* — Ophelia A Hawthorne
*Assistant Examiner* — Michael Milo
(74) *Attorney, Agent, or Firm* — Birch, Stewart, Kolasch & Birch, LLP

(57) ABSTRACT

This invention provides an adjustable oral interface for adapting a user's oral anatomy to deliver a negative pressure generated by an oral negative-pressure therapy system. The adjustable oral interface comprises a shield adapted for being situated between a user's lips and front teeth, a negative pressure deliverable part coupled with the shield, and a tube fluidly communicated between the negative pressure deliverable part and a negative pressure generation source. The negative pressure deliverable part is adapted for being adjustably situated at a space between the user's tongue and upper palate so as to be conformable to the contour of the upper palate, whereby the adjustable oral interface delivers negative pressure via the negative pressure deliverable part to the front and back of the user's oral cavity to eliminate air space between the tongue and the upper palate.

21 Claims, 20 Drawing Sheets

(58) Field of Classification Search
CPC ..... A61B 5/1072; A61B 5/1076; A61B 5/481;
A61B 5/4812; A61B 5/4818; A61B
5/4557; A61B 5/097; A61B 17/8071;
A63B 2071/086; A63B 71/085; A61C
7/08; A61C 7/36; A61C 9/0006; A61C
11/00; A61C 19/045; Y10S 602/902
USPC ......................................................... 128/848
See application file for complete search history.

(56) References Cited

U.S. PATENT DOCUMENTS

| | | | |
|---|---|---|---|
| 2009/0241969 A1 | 10/2009 | Walker | |
| 2011/0180076 A1* | 7/2011 | Hegde | A61F 5/566 128/848 |
| 2012/0234331 A1* | 9/2012 | Shantha | A61F 5/566 128/848 |
| 2013/0125902 A1* | 5/2013 | Danielian | A61B 17/24 128/859 |
| 2013/0213409 A1 | 8/2013 | Podmore et al. | |
| 2014/0034064 A1* | 2/2014 | Chen | A61M 16/0493 128/848 |
| 2014/0053851 A1* | 2/2014 | Podmore | A61F 5/566 128/848 |
| 2014/0190489 A1* | 7/2014 | Chen | A61F 5/566 128/848 |
| 2014/0190490 A1 | 7/2014 | Walker et al. | |

FOREIGN PATENT DOCUMENTS

| | | | | |
|---|---|---|---|---|
| CN | 104540480 A | | 4/2015 | |
| EP | 1 862 152 A1 | | 12/2007 | |
| EP | 2 301 490 A1 | | 3/2011 | |
| EP | 2301490 A1 | * | 3/2011 | ................ A61F 5/56 |
| EP | 2 881 090 A1 | | 6/2015 | |
| FR | 2929107 A1 | * | 10/2009 | ............. A61F 5/566 |
| JP | 2008-183388 A | | 8/2008 | |
| WO | WO 2014/110432 A2 | | 7/2014 | |
| WO | WO-2017192676 A1 | * | 11/2017 | ............. A61B 13/00 |

* cited by examiner

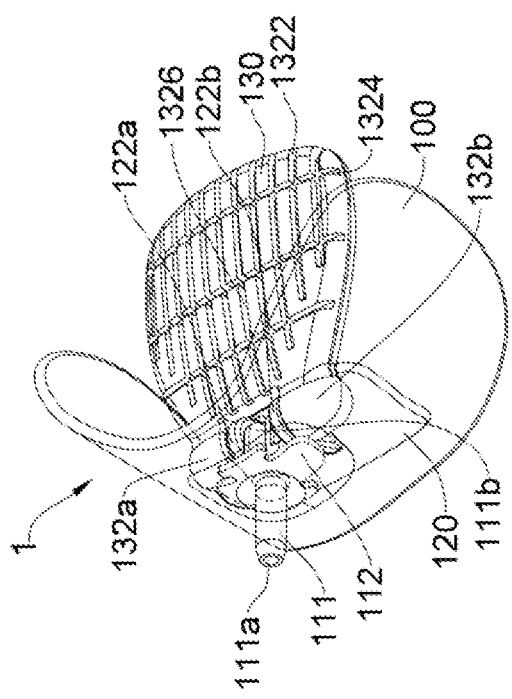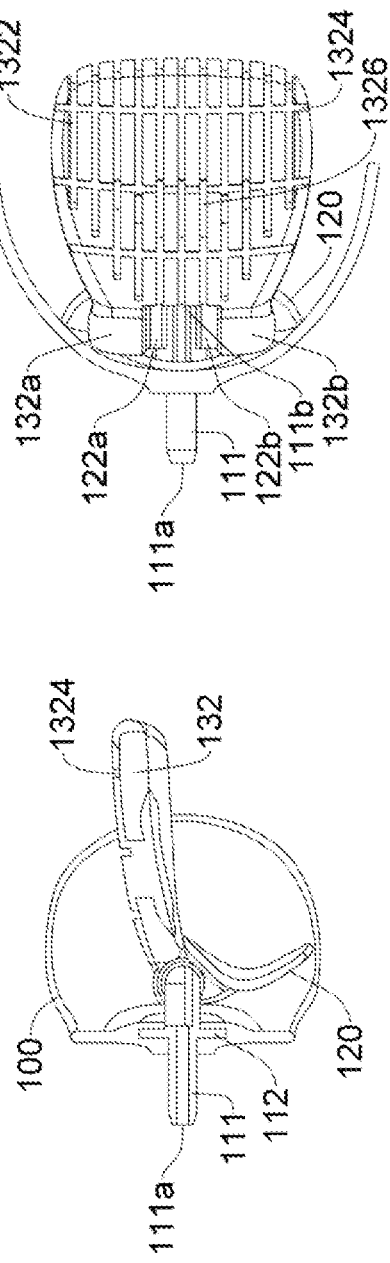

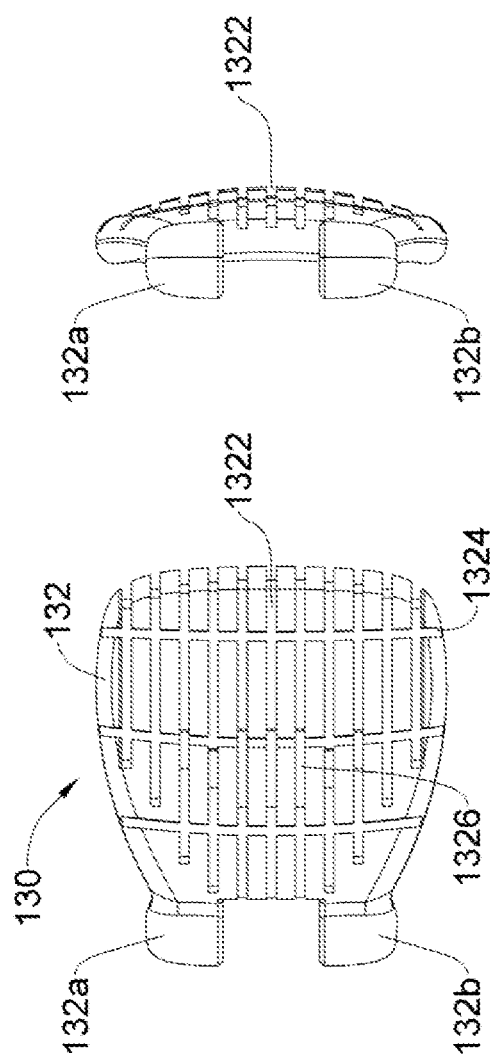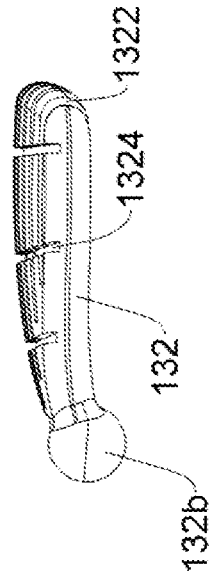

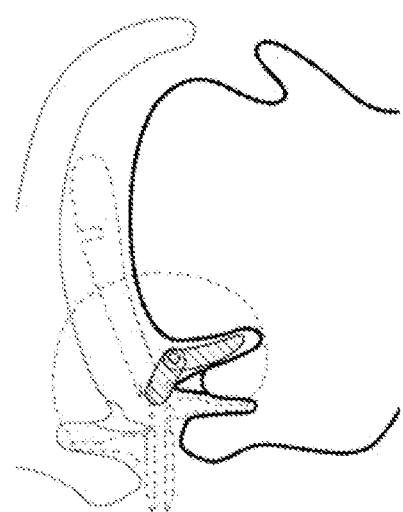
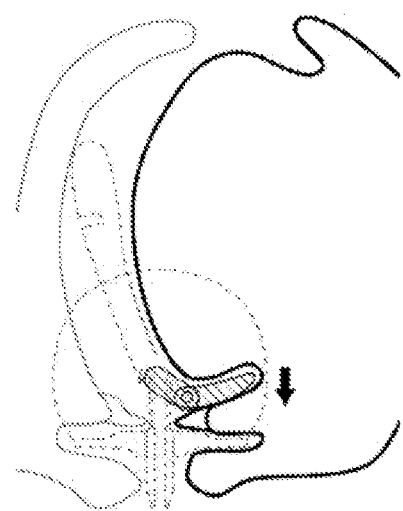
Fig. 7A
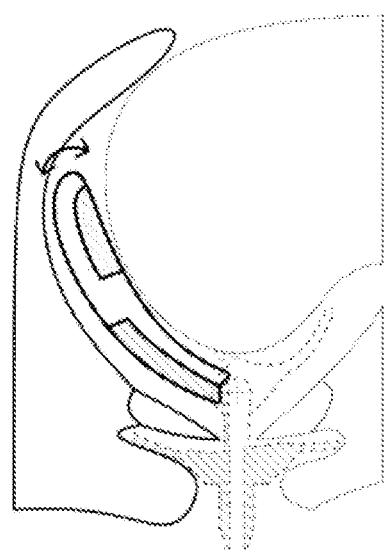
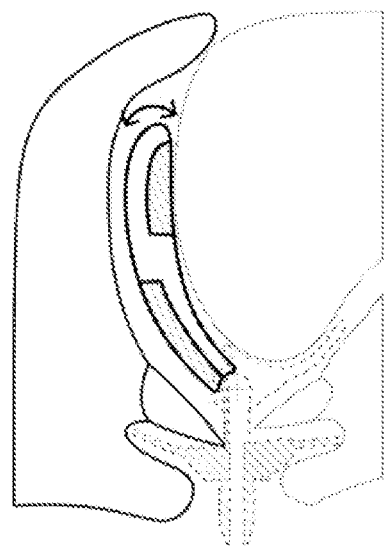
Fig. 7B

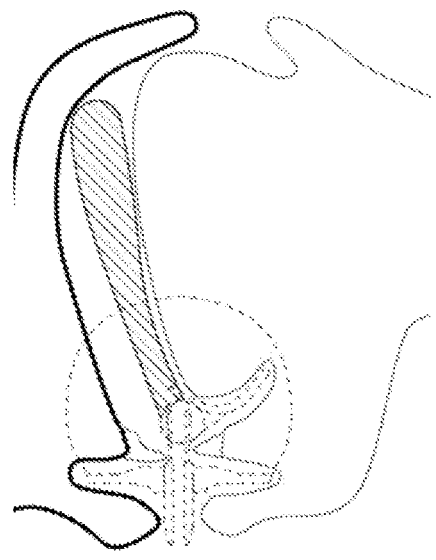
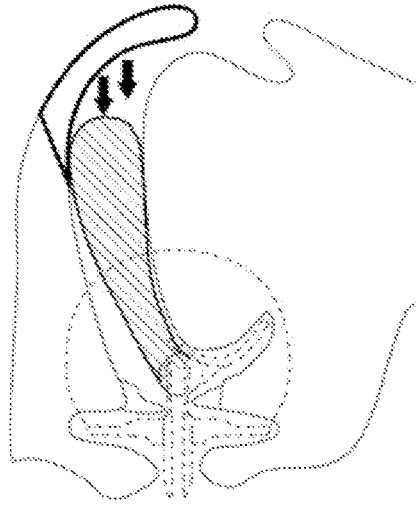
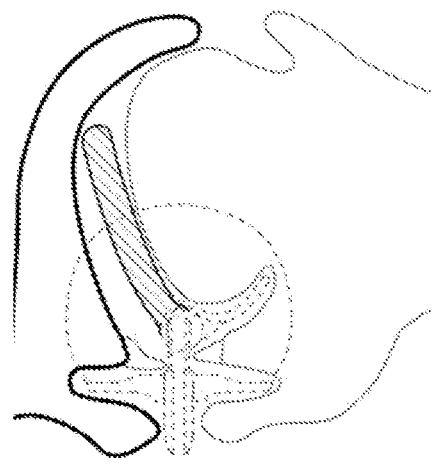
Fig. 7C
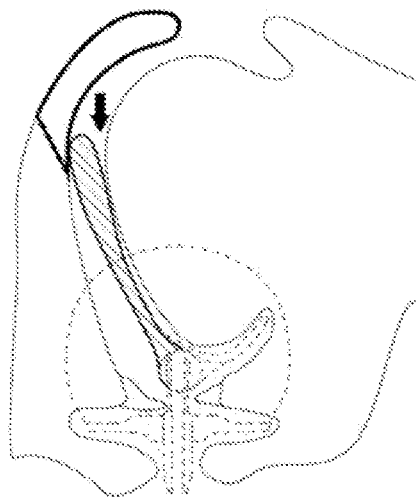
Fig. 7D

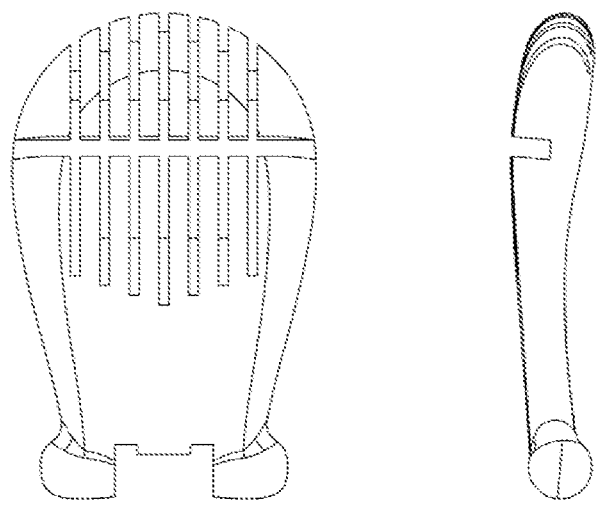
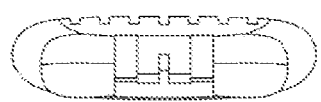
Fig. 10B
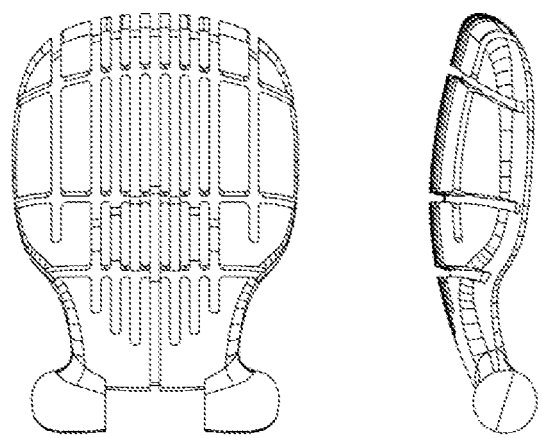
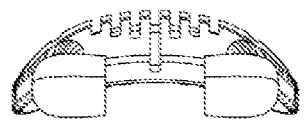
Fig. 10A

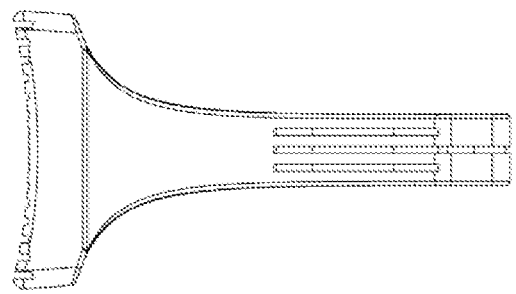
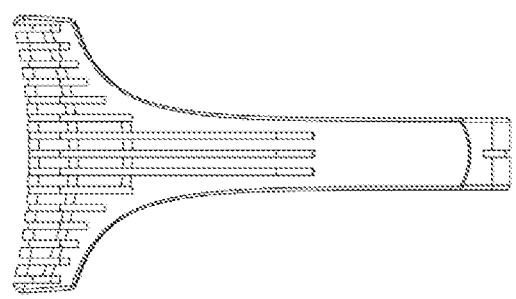
Fig. 10D
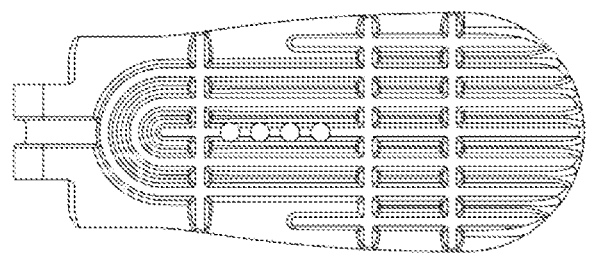
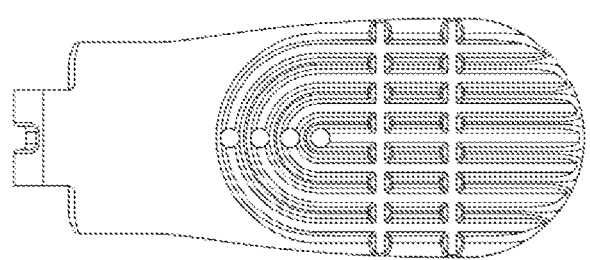
Fig. 10C

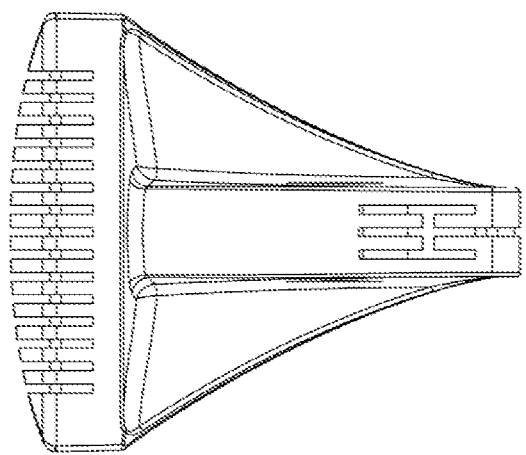
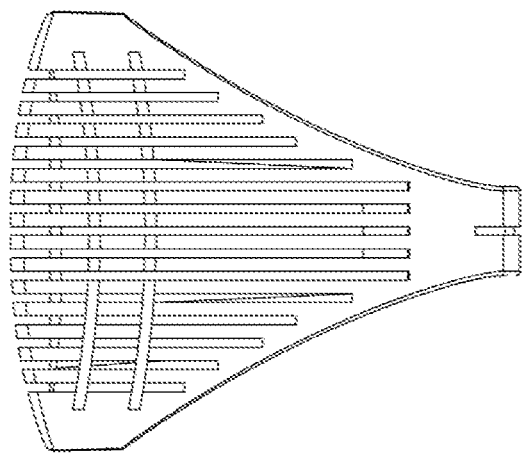
Fig. 10E

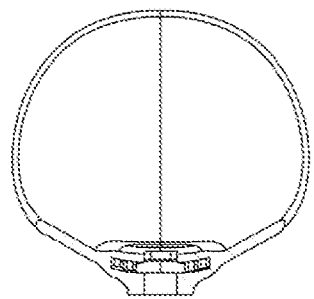
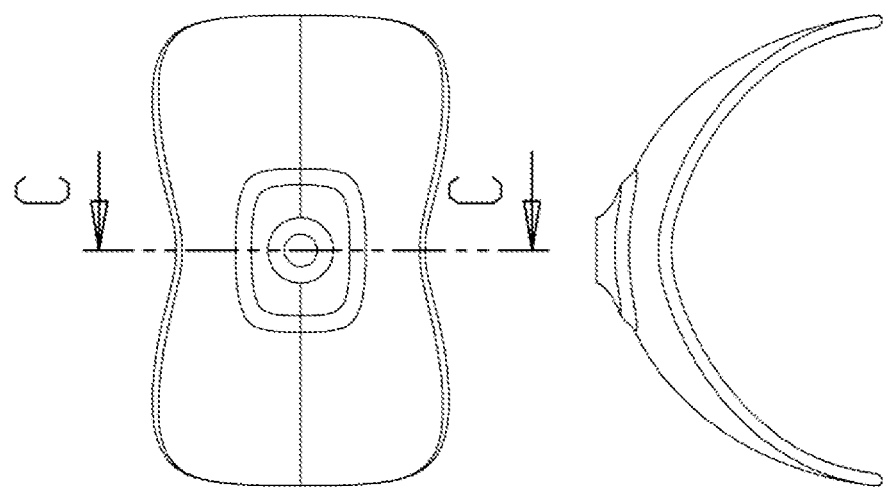
Fig. 12C

ADJUSTABLE ORAL INTERFACE FOR NEGATIVE-PRESSURE THERAPY SYSTEM

BACKGROUND OF THE INVENTION

Field of the Invention

The present invention relates to an oral negative-pressure therapy system, and more particularly, to an adjustable oral interface for the oral negative-pressure therapy system.

Prior Art

Obstructive sleep apnea (OSA), hypopnea, and upper airway resistance syndrome (UARS) are among a variety of known disorders characterized by episodes of complete or partial upper airway obstruction during such as sleep, anesthetization, or post anesthesia, OSA, hypopnea, and UARS cause intermittent interruption of ventilation during sleep with the consequence of potentially severe oxyhemoglobin desaturation. Typically, those afflicted with OSA, hypopnea, and/or UARS experience repeated, frequent arousal from sleep in response to the oxygen deprivation. The arousals result in sleep fragmentation and poor sleep continuity.

To treat such disorders, it has been proposed to apply a negative pressure to a user's oral cavity. For example, an appliance for treating obstructive sleep apnea (OSA) may utilize a device held in a patient's mouth where a vacuum is constantly drawn on the device in order to reposition portions of the patient's oral anatomy to reduce the likelihood of OSA. For example, the vacuum may be drawn in order to help draw the soft palate and/or rear portion of a patient's tongue away from the pharynx in order to maintain a clear breathing passage. In such devices held in a patient's mouth to deliver a negative pressure within the oral cavity, there is a possibility that the device cannot perfectly fit the patient's oral anatomy and reduce the efficacy or the comfort of the treatment. In order to improve the shortage, an adjustable oral interface may be provided to adapt to the patient's anatomy and insure the efficacy.

SUMMARY OF THE INVENTION

In one aspect, an adjustable oral interface for adapting a user's oral anatomy to deliver a negative pressure generated by an oral negative-pressure therapy system is disclosed. The adjustable oral interface includes a shield adapted for being situated between a user's lips and front teeth, a negative pressure deliverable part coupled with the shield, and a tube fluidly communicated between the negative pressure deliverable part and a negative pressure generation source, wherein the negative pressure deliverable part is adapted for adjustably being situated at a space between the user's tongue and upper palate so as to be conformable to the contour of the upper palate, whereby the adjustable oral interface delivers negative pressure via the negative pressure deliverable part to the front and back of the user's oral cavity to eliminate air space between the tongue and the upper palate.

In one aspect, an adjustable oral interface may include a shield adapted for being situated between a user's lips and front teeth, a negative pressure deliverable part coupled with the shield, a tube fluidly communicated between the negative pressure deliverable part and a negative pressure generation source, and a body connector coupled to the shield and fluidly connected between the negative pressure deliverable part and the tube. The body connector is provided with an axis for pivotally assembling the negative pressure deliverable part to the body connector. The negative pressure deliverable part is to be adjustably situated at the space between the user's tongue and upper palate so as to be conformable to the contour of the user's upper palate, whereby the adjustable oral interface delivers negative pressure via the negative pressure deliverable part to both front and back of the oral cavity to eliminate air space between the tongue and the upper palate. Further, the negative pressure deliverable part is configurable by different sizes, different diameters and different shapes, and it is detachable and interchangeable to accommodate different oral anatomy of users. The shield to be situated between the user's lips and front teeth functions as a seal. Additionally, the shield is configurable by different sizes and different shapes, and it is detachable and interchangeable to accommodate oral anatomy of different users. Each of the parts of the adjustable oral interface is individually detachable and interchangeable and easy to clean and/or be replaced.

In one aspect, an adjustable oral interface may include a shield adapted for being situated between a user's lips and front teeth, a negative pressure deliverable part coupled with the shield, a tube fluidly communicated between the negative pressure deliverable part and a negative pressure generation source, a body connector coupled to the shield and fluidly connected between the negative pressure deliverable part and the tube. The body connector is provided with an axis for pivotally assembling the negative pressure deliverable part to the body connector. The adjustable oral interface also comprises a tongue protector pivotally assembled to the axis of the body connector. The negative pressure deliverable part is adjustably situated between the space between the user's tongue and upper palate so as to be conformable to the contour of the user's upper palate, whereby the adjustable oral interface delivers negative pressure via the negative pressure deliverable part to the front and back of the user's oral cavity to eliminate air space between the tongue and the upper palate. Further, the negative pressure deliverable part is configurable by different sizes, different diameters and different shapes, and it is detachable and interchangeable to accommodate oral anatomy of different users. The shield to be situated between the user's lips and front teeth functions as a seal. The shield is configurable by different sizes and different shapes, and it is detachable and interchangeable to accommodate oral anatomy of different users. The tongue protector is configurable by different sizes and different shapes, and it is also detachable and interchangeable to accommodate oral anatomy of different users. Each of the parts of the adjustable oral interface is individually detachable and interchangeable and easy to clean and/or be replaced. The body connector serves as an axis to assemble the other parts and as an anchor of the alignment of the upper and lower teeth.

The shield can be made of thermoplastic materials which can be remolded through compression on the front teeth and formed a configuration which fits the anatomy features of the user. The negative pressure deliverable part can be made of thermoplastic materials and compression remolded to contour the space between the tongue and upper palate. The thermoplastic materials having remolding effect used in the present invention may be, for example, thermoplastic elastomers (briefly named TPE), ethylene vinyl acetate (briefly named EVA) etc. Further, the negative pressure deliverable part can be made of elastic porous materials which allow the negative pressure flow through the negative pressure deliverable part.

The negative pressure deliverable part comprises one or more open fluid channels on a surface thereof. The one or more of open fluid channels occupies an area ratio of the negative pressure deliverable part benefits a negative pressure delivery efficacy. In one implementation, the one or more open fluid channels are configured and arranged in an upper surface of the negative pressure deliverable part in an isometric pattern. In one implementation, the one or more of open fluid channels are configured in parallel with a longitudinal axis of the negative pressure deliverable part. In one implementation, the one or more of open fluid channels are configured in parallel with a longitudinal axis of the negative pressure deliverable part. In one implementation, the one or more of open fluid channels is perpendicular to a longitudinal axis of the negative pressure deliverable part. In one implementation, the negative deliverable part is in a form of one of streamline, oval, and water drop. In one implementation, the negative pressure deliverable part is configured to fit a shape of the space between the user's tongue and hard palate. In one implementation, the negative pressure deliverable part has a front end in proximity to the user's tongue tip and a rear end in proximity to the user's soft palate, wherein a thickness of the rear end is larger than a thickness of the front end.

The negative pressure deliverable part has one or more through holes fluidly communicated upper and lower surfaces of the negative pressure deliverable part.

In one aspect, the adjustable oral interface for adapting the user's oral anatomy to deliver a negative pressure which is −10~−150 mmHg is disclosed. Particularly, the negative pressure is −20~−100 mmHg. More Particularly, the negative pressure is −30~−60 mmHg.

In one aspect, the adjustable oral interface for adapting the user's oral anatomy to deliver a negative pressure which is with a flow rate between 10 ml/min~800 ml/min. Particularly, the flow rate is between 30 ml/min~600 ml/min. More particularly, the flow rate is between 50 ml/min~300 ml/min.

In one aspect, the body connector is made of hard polymers, for example polycarbonate (briefly named PC), polypropylene (briefly named PP), or other hard materials. The shield, negative pressure deliverable part, tube and tongue protector are made of soft polymeric elastomers. Particularly, the soft polymeric elastomers comprise thermoplastic elastomers (briefly named TPE), ethylene vinyl acetate (briefly named EVA), silicone or other soft and elastic materials.

The adjustable oral interface for adapting the user's oral anatomy to deliver a negative pressure can be organized with an optional product module comprising the selected parts and the suitable pressure and flow rate.

BRIEF DESCRIPTION OF THE DRAWINGS

FIG. 2A is a schematic perspective view of the adjustable oral interface of the first embodiment; FIG. 2B is a schematic cross-sectional side view of the adjustable oral interface of the first embodiment; and FIG. 2C is a schematic top view of the adjustable oral interface of the first embodiment.

FIG. 3A is a schematic top view of a negative pressure deliverable part of the adjustable oral interface of the first embodiment; FIG. 3B is a schematic side view of the negative pressure deliverable part of the adjustable oral interface of the first embodiment; and FIG. 3C is a schematic front view of the negative pressure deliverable part of the adjustable oral interface of the first embodiment.

FIG. 7A is schematic views showing a tongue protector of an adjustable oral interface of the present invention that is how to control a forward movement of a user's lower mandible.

FIG. 7B is schematic views showing a position of a negative pressure deliverable part of an adjustable oral interface of the present invention is adjustable for adapting oral anatomy of different users.

FIG. 7C is schematic views showing a length of a negative pressure deliverable part of an adjustable oral interface of the present invention is selected based on oral anatomy of different users.

FIG. 7D is schematic views of a variance of a negative pressure deliverable part of an adjustable oral interface of the present invention, in which a thickness of a rear end of the negative pressure deliverable part is larger than a thickness of its front end.

FIG. 10A to FIG. 10F show several variances of a negative pressure deliverable part of an adjustable oral interface of the present invention.

FIG. 12A to FIG. 12C show several variances of a shield of an adjustable oral interface of the present invention.

DETAILED DESCRIPTION OF PREFERRED EMBODIMENTS OF THE INVENTION

Figure 1:
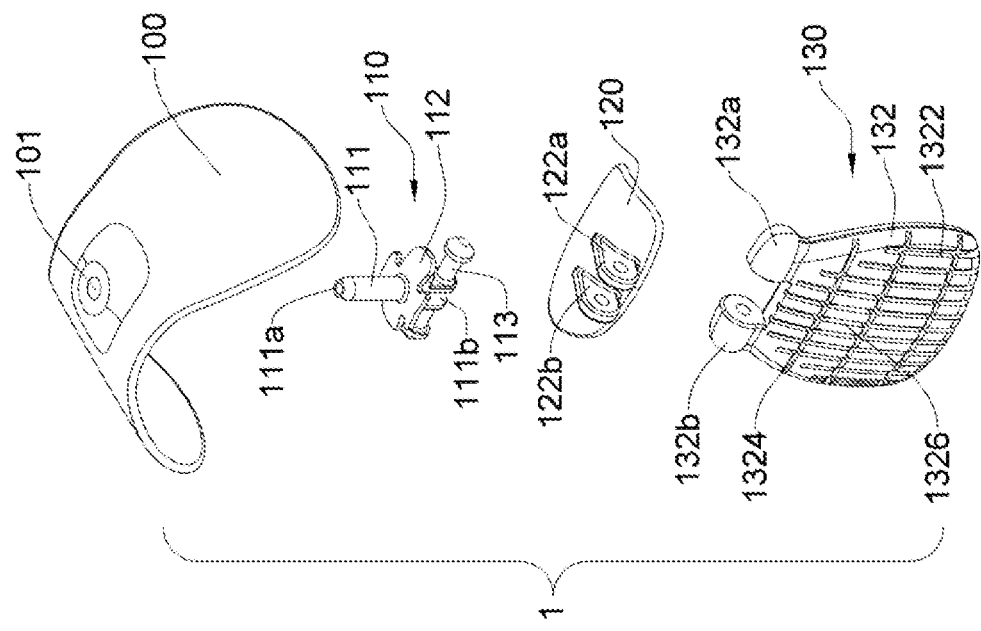
FIG. 1 is a schematic exploded perspective view of an adjustable oral interface according to a first embodiment of the present invention.

The purpose of following embodiments with reference to accompanying drawings is to explain and illustrate the present invention. It should be noted that the following embodiments and accompanying drawings is intended to be illustrative but not limiting. An ordinarily skill person in the art should understand similar structure feature may be called in different terms in the field. Hence, any structure has similar function as the structure feature described in the present invention should be included in the scope of the present disclosure. The drawings of the embodiments/variances of the present invention are not necessarily conform to the sizes and dimension ratios of actual structures, and more specifically, some features may be magnified or scaled down to show details of particular components. Besides, the accompanying drawings may be simplified for clarity, for example, each part and/or portion and/or detailed structure of a given apparatus may not be plotted in the accompanying drawings.

FIG. 1, FIG. 2A, FIG. 2B and FIG. 2C illustrate schematic exploded perspective view, perspective view, cross-sectional side view and top view of an adjustable oral interface of a negative-pressure therapy system according to a first embodiment of the present invention. Please refer to these drawings, an adjustable oral interface 1 includes a shield 100, a body connector 110, a tongue protector 120 and a negative pressure deliverable part 130. The shield 100 is adapted for being situated between a user's lips and front teeth such that a through hole 101 provided in a central region of the shield 100 is attached onto an inner surface of the user's lips. The central region of the shield 100 includes an accommodation space that the through hole 101 passes through. The body connector 110 includes a hollow tube 111, an engaging piece 112 and an axis 113. A front end 111a of the hollow tube 111 of the body connector 110 air-tightly passes the through hole 101 of the shield 100 and extends out of the shield 100 to fluidly connect to a fluid conduit (not shown in the drawings) that is adapted for being fluidly communicated between a negative pressure generation source and the hollow tube 111. The engaging piece 112 of the body connector 110 is engaged into the accommodation space formed in the central region of the shield 100, and a rear end 111b of the hollow tube 111 opposite to its front end 111a is positioned at a back surface of the shield 100. The rear end 111b of the hollow tube 111 is formed of a top-opened fluid channel positioned behind the engaging piece 112. The axis 113 of the body connector 110 is disposed at the rear end 111b of the hollow tube 111 and extending out of outer surfaces of two opposite lateral walls of the top-opened fluid channel at the rear end 111b of the hollow tube 111, and the axis 113 is perpendicular to the hollow tube 111. The tongue protector 120 includes a pair of hanging ears 122a, 122b. The hanging ears 122a, 122b pivotally pass through the axis 113 of the body connector 110 and resisting against the outer surfaces of the two opposite lateral walls of the top-opened fluid channel at the rear end 111b of the hollow tube 111, whereby the tongue protector 120 is position-adjustably assembled to the body connector 110. The negative pressure deliverable part 130 includes a body 132 and a pair of ears 132a, 132b. The pair of the ears 132a, 132b are oppositely formed at a front portion of the body 132 and being individually pivotally assembled to two opposite ends of the axis 113 of the body connector 110 to engage the pair of hanging ears 122a, 122b of the tongue protector 120 resisting against the axis 113 in order that the tongue protector 120 is assembled beneath the negative pressure deliverable part 130, and the negative pressure deliverable part 130 is position-adjustably assembled to the body connector 110. As shown in FIG. 2A, the components of the adjustable oral interface 1, such as the shield 100, the tongue protector 120 and the negative pressure deliverable part 130, are assembled together by the body connector 110. The tongue protector 110 and the negative pressure deliverable part 130 can be adjusted around the axis 113 to optimum positions for adapting the oral anatomy of the user. The shield 100, tongue protector 120 and the negative pressure deliverable part 130 of the adjustable oral interface 1 are individually detachable and interchangeable and easy to clean and/or be replaced. Even after detached from the adjustable oral interface 1, these parts also can be assembled together again.

Please refer to FIG. 2C and FIG. 3A to FIG. 3C, a top surface of the negative pressure deliverable part 130 is provided with a plenty of trench-shaped longitudinal open fluid channels 1322 extending from a front end of the body 132 to its rear end in a longitudinal axis direction. The longitudinal open fluid channels 1322 fluidly communicate with the top-opened fluid channel formed at the rear end 111b of the hollow tube 111 of the body connector 110. As shown in FIG. 2C, preferably, the longitudinal open fluid channels 1322 are arranged in an isometric pattern and parallel to each other on the top surface of the body 132 of the negative pressure deliverable part 130. The top surface of the negative pressure deliverable part 130 further includes a plenty of trench-shaped traverse open fluid channels 1324 extending from a left side of the body 132 to its right side in a traverse axis direction. The traverse open fluid channels 1324 interdigitate and fluidly communicate with the longitudinal open fluid channels 1322. Preferably, the traverse open fluid channels 1324 are arranged in an isometric pattern and parallel to each other on the top surface of the body 132 of the negative pressure deliverable part 130, and they are perpendicular to the longitudinal open fluid channels 1322. The negative pressure deliverable part 130 further comprises a plurality of through openings 1326 passing through the top and bottom surfaces of the body 132. Preferably, the through openings 1326 individually pass through the longitudinal open fluid channels 1322 and fluidly communicate with the top and bottom surfaces of the body 132. Optionally, the through openings 1326 may be designed to pass through the traverse open fluid channels 1324 (not shown in the drawings) and fluidly communicate with the top and bottom surfaces of the body 132.

Figure 5A:
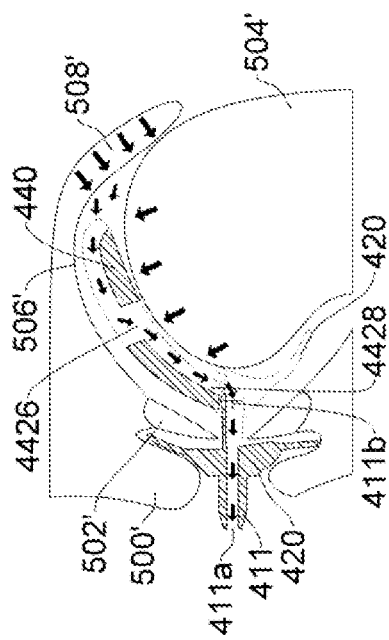
FIG. 5A is a schematic view showing a negative pressure delivery path through the adjustable oral interface of the first embodiment.

Please refer to FIG. 5A, when the oral adjustable interface 1 is worn in the oral cavity of a user, the shield 100 is situated between the user's lips 500 and front teeth 502, whereby the rear end 111b of the hollow tube 111 of the body connector 110 extends in the oral cavity of the user, and the negative pressure deliverable part 130 is position-adjustably situated at the space between the user's tongue 504 and upper palate 506 to be conformable to the contour of the user' upper palate, and the tip of the user's tongue 504 resists against an inner surface of the tongue protector 120. The top-opened fluid channel at the rear end 111*b* of the hollow tube 111 of the body connector 110 fluidly communicates with the longitudinal open fluid channels 1322 and traverse open fluid channels 1324 formed on the top surface of the negative pressure deliverable part 130 and the through openings 1326. The negative pressure generation source (not shown in the drawings) sucks vacuum from the adjustable oral interface 1 via the fluid conduit connected to the front end 111*a* of the hollow tube 111 of the body connector 110 in order that negative pressure delivery paths as flow directions represented by arrows are constituted in the user's oral cavity as shown in FIG. 5A. In other words, the air at the space from the front to the back of the oral cavity between the user's upper palate and the negative pressure deliverable part 130 is delivered to the front end of the negative pressure deliverable part 130 via the longitudinal open fluid channels 1322 and traverse open fluid channels 1324 on the top surface of the negative pressure deliverable part 130. The air between the tongue 504 and the negative pressure deliverable part 130 from the front to the back of the oral cavity is delivered to the top surface of the negative pressure deliverable part 130 via the through openings 1326 of the negative pressure deliverable part 130, and then delivered to the front end of the negative pressure deliverable part 130 via the longitudinal open fluid channels 1322 and traverse open fluid channels 1324 on the top surface of the negative pressure deliverable part. The air in the oral cavity delivered to the front end of the negative pressure deliverable part 130 are drawn out of the oral cavity via the top-opened fluid channel at the rear end 111*b* of the hollow tube 111 of the body connector 110 to eliminate air space between the tongue and the upper palate. As a consequence, negative pressure is delivered to the front and back regions of the oral cavity via the negative pressure deliverable part 130. The negative pressure at the front of the oral cavity lifts the tip of the tongue 504 upwardly to make the rear portion of the tongue 504 far away from the back wall of the upper airway, and the negative pressure at the back of the oral cavity pulls the soft palate 508 to engage against the rear portion of the tongue 504 so that the soft palate 508 is far away from the back wall of the upper airway. A patency of the upper airway patency is obtained and maintained.

When in use, the shield 100 of the adjustable oral interface 1 can function as a seal to prevent the user's oral cavity from air leakage. In an implementation, the shield 100 is flexibly conformable to the contours of the inner surface of the lips and the outer surface of the front teeth of the user to attain the air-tight effect. In another implementation, the shield 100 is configured as a thin piece, particularly, the shape of the shield 100 is configured to adapt the space between the inner surface of the lips and the outer surface of the front teeth of the user. In another implementation, the length of the shield 100 is 10 mm to 120 mm from its left side to its right side. Herein, the direction of the left side to the right side of the shield 100 is along the teeth arrangement direction from the left-side face to the right-side face of the user when the adjustable oral interface 1 is in use. In another implementation, the shield 100 can be made of thermoplastic materials which can be remolded through compression on the front teeth and formed a configuration which fits the anatomy features of the user.

Figure 6A:
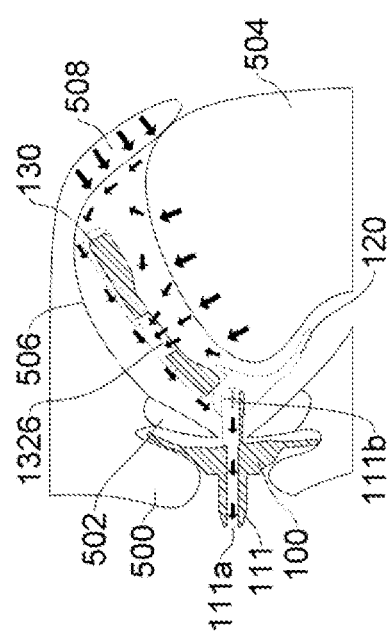
FIG. 6A is a schematic perspective view showing position adjustment of a negative pressure deliverable part and a tongue protector of an adjustable oral interface of the present invention.
Figure 6B:
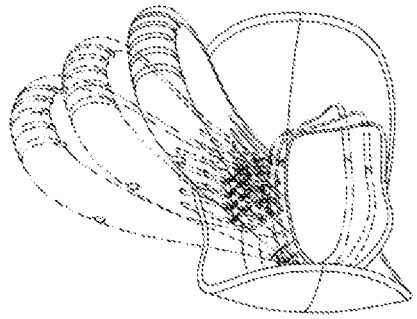
FIG. 6B is a schematic cross sectional side view of FIG. 6A.

Please refer to FIG. 6A and FIG. 6B as an illustration, the negative pressure deliverable part 130 can be pivoted around the axis 113 of the body connector 110 to change and adjust its position in relative to the axis 113 and hence fits the oral anatomy of the user, whereby the negative pressure deliverable part 130 can be conformable to the contour of the upper palate of the user. The tongue protector 120 of the adjustable oral interface 1 also can be pivoted around the axis 113 of the body connector 110 to change and adjust its position in relative to the axis 113 and hence fits the oral anatomy of the user. In other words, the position adjustment mechanisms of the negative pressure deliverable part 130 and the tongue protector 120 of the adjustable oral interface 1 facilitate the adjustable oral interface 1 to fit the oral anatomy of different users to prohibit the user uncomfortable.

The negative pressure from the negative pressure generation source is changeable and adjustable to improve the user's comfort during the negative pressure therapy period. For example, the negative pressure from the negative pressure generation source is $-10$~$-150$ mmHg. Particularly, the negative pressure is $-20$~$-100$ mmHg. More particularly, the negative pressure is $-30$~$-60$ mmHg.

The shield 100, tongue protector 120 and the negative pressure deliverable part 130 can be made of soft polymeric elastomers, for example thermoplastic elastomers (briefly named TPE), ethylene vinyl acetate (briefly named EVA), silicone etc., or other soft and elastic materials. The body connector 110 can be made of hard polymers, for example polycarbonate (briefly named PC), polypropylene (briefly named PP) etc., or other hard materials.

Figure 4A:
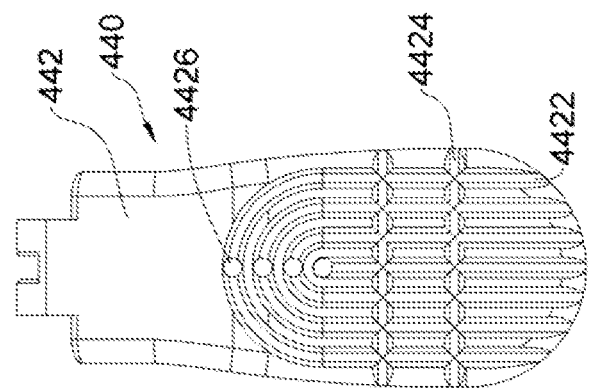
FIG. 4A is a schematic top view of a negative pressure deliverable part of the adjustable oral interface of the second embodiment.
Figure 4:
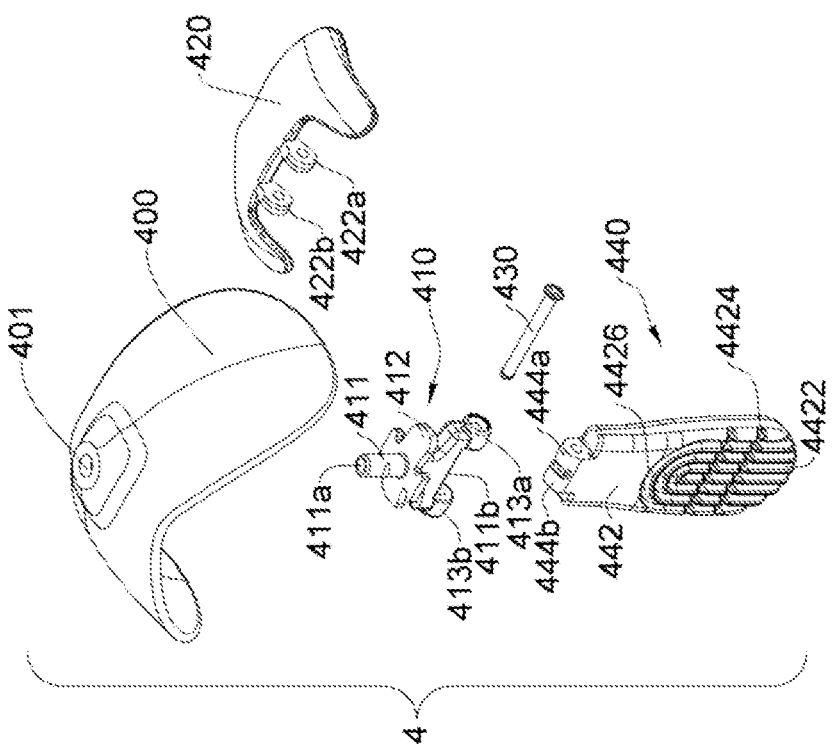
FIG. 4 is a schematic exploded perspective view of an adjustable oral interface according to a second embodiment of the present invention.
Figure 5B:
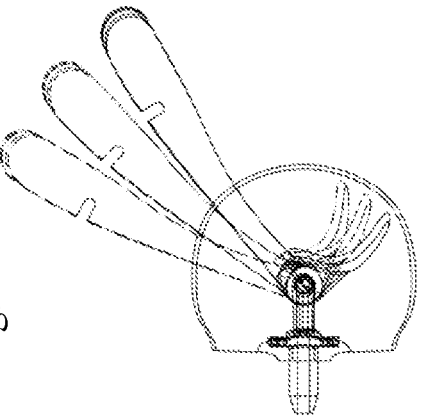
FIG. 5B is a schematic view showing a negative pressure delivery path through the adjustable oral interface of the second embodiment.

FIG. 4 is a schematic exploded perspective view of an adjustable oral interface 4 according to a second embodiment of the present invention. The adjustable oral interface 4 includes a shield 400, a body connector 410, a tongue protector 420, a pivot pin 430 and a negative pressure deliverable part 440. The shield 400 is adapted for being situated between a user's lips and front teeth such that a through hole 401 provided in a central region of the shield 400 is attached onto an inner surface of the user's lips. The central region of the shield 400 includes an accommodation space that the through hole 401 passes through. The body connector 410 includes a hollow tube 411, an engaging piece 412 and a pair of holes 413*a*, 413*b* for the pivot axis 430 passing through. A front end 411*a* of the hollow tube 411 of the body connector 410 air-tightly passes the through hole 401 and extends out of the shield 400 to fluidly connect to a fluid conduit (not shown in the drawings). The fluid conduit fluidly communicates between a negative pressure generation source and the hollow tube 411. A rear end 411*b* of the hollow tube 411 is formed of a bottom-opened fluid channel behind the engaging piece 412 as shown in FIG. 5B. The holes 413*a*, 413*b* of the body connector 410 are opposely formed at the rear end 411*b* of the hollow tube 411. A front end of the tongue protector 420 is provided with a pair of hanging ears 422*a*, 422*b*. The negative pressure deliverable part 440 includes a body 442 and a pair of ears 444*a*, 444*b*. The ears 444*a*, 444*b* are opposely formed at the front end of the body 442. The pivot pin 430 sequentially passes through the hole 413*a*, the hanging ear 422*a* of the tongue protector 420, the ears 444*a*, 444*b* of the negative pressure deliverable part 440 and the ear 422*b* of the tongue protector 420 and the hole 413*b* of the body connector 410 to assemble the tongue protector 420 and the negative pressure deliverable part 440 to the body connector 410, and the tongue protector 420 is beneath the negative pressure deliverable part 440. In an implementation, each of the two opposite ends of the axis pin 430 is provided with an elastic engaging block (not shown in the drawings) in order that the axis pin 430 can engage with the body connector 410 once the axis pin 430 passes the holes 413a, 413b. In other words, the user needs to destroy the engaging blocks if he/she wants to detach the tongue protector 420 and the negative pressure deliverable part 440 from the adjustable oral interface 4. Once the tongue protector 420 and the negative pressure deliverable part 440 are to be assembled to the adjustable oral interface 4 again, an undamaged axis pin 430 is needed for the tongue protector 420 and the negative pressure deliverable part 440 passing through. Both of the tongue protector 420 and the negative pressure deliverable part 440 can pivot around the axis pin 430 for position adjustment (for example, as shown in FIG. 6A and FIG. 6B) to adapt the oral anatomy of different users. Therefore, the adjustable oral interface 4 can fit the oral anatomy of different users to avoid the user uncomfortable.

Figure 4B:
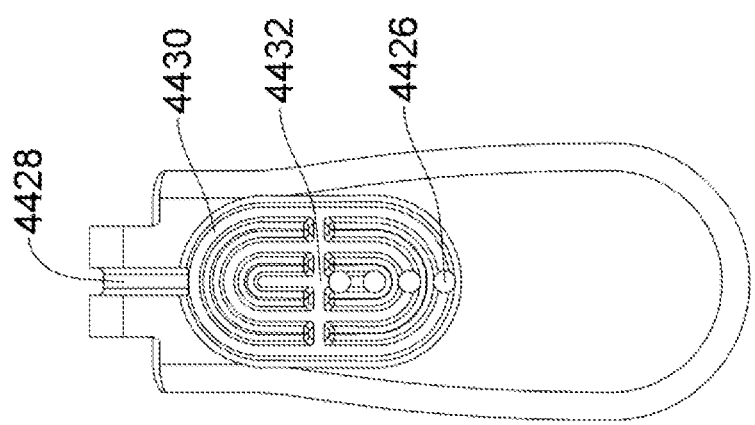
FIG. 4B is a schematic bottom view of the negative pressure deliverable part of the adjustable oral interface of the second embodiment.

Please refer to FIG. 4A, a top surface of the negative pressure deliverable part 440 is provided with a plenty of trench-shaped open loop fluid channels 4422 each of which beginning from a position of a rear side of the body 442 longitudinally extends to a place corresponding to one fourth to one third portion of the hard palate forward from a rear end of the hard palate when the adjustable oral interface 4 being worn in the user's oral cavity, and then reversely extends to an opposite position of the rear side of the body 442 to constitute a loop with a closed end far away from the rear side of the body 442 and an open end at the rear side of the body 442. Preferably, the open loop fluid channels 4422 are arranged at the top surface of the body 442 of the negative pressure deliverable part 440 in an isometric pattern and in parallel with each other. The top surface of the negative pressure deliverable part 440 further includes, for example, a plenty of trench-shaped traverse open fluid channels 4424 extending from a left side of the body 442 to a right side of the body 442 along a traverse axis direction. The traverse open fluid channels 4424 are fluidly communicately interdigitated with the open loop fluid channels 4422. Preferably, the traverse open fluid channels 4424 are arranged at the top surface of the body 442 of the negative pressure deliverable part 440 and perpendicular to the open loop fluid channels 4422. The negative pressure deliverable part 440 further includes a plurality of through openings 4426 passing through the top and bottom surfaces of the body 442. Preferably, the through openings 4426 are positioned in proximity with the closed ends of the open loop fluid channels 4422 and passing through the open loop fluid channels 4422 and fluidly communicately the top and bottom surfaces of the body 442. The bottom surface of the body 442 of the negative pressure deliverable part 440 further includes a longitudinal open fluid channel 4428, a trench-shaped loop fluid channel 4430 and a trench-shaped traverse open fluid channel 4432. The loop fluid channel 4430 are arranged in a concentric and isometric pattern. Each of the through openings 4426 passes through a pair of the open loop fluid channel 4422 and the loop fluid channel 4430 corresponding to each other. The traverse open fluid channel 4432 extends at the bottom surface of the body 442 between the left side and right side of the body 442 along a traverse axis direction. The traverse open fluid channel 4432 is fluidly communicately interdigitated with the loop fluid channel 4430. The longitudinal open fluid channel 4428 longitudinally extends from a front end of the bottom surface of the body 442 to the outermost loop fluid channel 4430 and being fluidly communicated between the outermost loop fluid channel 4430 and the bottom-opened fluid channel at the rear end 411b of the body connector 410 (please see FIG. 4B and FIG. 5B). The trench-shaped loop fluid channels 4430 arranged in a concentric pattern at the bottom surface of the negative pressure deliverable part 440 are positioned at a rear end of the longitudinal open fluid channel 4428 in proximity with the tongue tip of the user when the adjustable oral interface 4 is worn in the user's oral cavity.

Please refer to FIG. 5B, when the adjustable oral interface 4 is in use, the shield 400 is situated between the user's lips 500' and front teeth, and the bottom-opened fluid channel at the rear end 411b of the hollow tube 411 of the body connector 410 extends in the oral cavity, the negative pressure deliverable part 440 is adjustably placed between the tongue 504' and the upper palate 506' to be comfortable to the contour of the upper palate, and the tip of the tongue 504' resists against an inner surface of the tongue protector 420. The bottom-opened fluid channel at the rear end 411b of the hollow tube 411 of the body connector 410 fluidly communicates with the longitudinal open fluid channel 4428, loop fluid channels 4430, traverse open fluid channel 4432 at the bottom surface of the negative pressure deliverable part 440, through openings 4426 and open loop fluid channels 4422, traverse open fluid channels 4424 at the top surface of the negative pressure deliverable part 440, whereby the negative pressure is delivered to the hard palate via the open loop fluid channels 4422 and the traverse open fluid channels 4424 at the top surface of the negative pressure deliverable part 440, and then the negative pressure is delivered to the tongue tissue through the loop fluid channels 4430 and the traverse open fluid channel 4432 at the bottom surface of the negative pressure deliverable part 440. The negative pressure generation source (not shown in the drawings) sucks vacuum from the adjustable oral interface 4 via the fluid conduit connected to the front end 411a of the hollow tube 411 of the body connector 410 in order that negative pressure delivery paths as flow directions represented by arrows are constituted in the user's oral cavity as shown in FIG. 5B. In other words, the air at the space from the front to the back of the oral cavity between the user's upper palate and the negative pressure deliverable part 440 is delivered to the front end of the negative pressure deliverable part 440 via the open loop fluid channels 4422 and traverse open fluid channels 4424 at the top surface of the negative pressure deliverable part 440, through openings 4426 and the longitudinal open fluid channel 4428. The air between the tongue 504' and the negative pressure deliverable part 440 from the front to the back of the oral cavity is delivered to the front end of the negative pressure deliverable part 440. The air delivered to the front end of the negative pressure deliverable part 440 is drawn out from the oral cavity via the bottom-opened fluid channel at the rear end 411b of the hollow tube 411 of the body connector 410 to eliminate air space between the tongue and the upper palate. As a consequence, negative pressure is delivered to the front and back regions of the oral cavity via the negative pressure deliverable part 440. The negative pressure at the front of the oral cavity lifts the tip of the tongue 504' upwardly to make the rear portion of the tongue 504' far away from the back wall of the upper airway, and the negative pressure at the back of the oral cavity pulls the soft palate 508' to engage against the rear portion of the tongue 504' so that the soft palate 508' is far away from the back wall of the upper airway. A patency of the upper airway patency is obtained and maintained.

Moreover, the negative pressure is evenly distributed among the tongue, the upper palate and the soft palate with the adjustable oral interface 4 delivering negative pressure via the body connector 410, the open loop fluid channels 4422 and the traverse open fluid channels 4424 at the top surface of the negative pressure deliverable part 440, through openings 4426, and the longitudinal open fluid channel 4428, the loop fluid channels 4430 and the traverse open fluid channel 4432 at the bottom surface of the negative pressure deliverable part 440 such that the tongue tissue and soft palate are firmly stabilized to keep airway patency of the user.

When in use, the shield 400 of the adjustable oral interface 4 functions as a seal to prevent the user's oral cavity from air leakage. In an implementation, the shield 400 can be made of thermoplastic materials which can be remolded through compression on the front teeth and formed a configuration which fits the anatomy features of the user.

Please refer to FIG. 6A and FIG. 6B as an illustration, the negative pressure deliverable part 440 of the adjustable oral interface 4 can be pivoted around the axis pin 430 of the body connector 410 to change and adjust its position in relative to the axis pin 430 and hence fits the oral anatomy of the user, whereby the negative pressure deliverable part 440 can be conformable to the contour of the upper palate of the user. The tongue protector 420 of the adjustable oral interface 4 also can be pivoted around the axis pin 430 of the body connector 410 to change and adjust its position in relative to the axis pin 430 and hence fits the oral anatomy of the user. In other words, the position adjustment mechanisms of the negative pressure deliverable part 440 and the tongue protector 420 of the adjustable oral interface 4 facilitate the adjustable oral interface 4 to fit the oral anatomy of different users to prohibit the user uncomfortable.

Depending on the use of the adjustable oral interface 4, the negative pressure from the negative pressure generation source is changeable and adjustable to improve the user's comfort during the negative pressure therapy period. For example, the negative pressure from the negative pressure generation source is −10∼−150 mmHg. Particularly, the negative pressure is −20∼−100 mmHg. More particularly, the negative pressure is −30∼−60 mmHg.

The shield 400, tongue protector 420 and the negative pressure deliverable part 440 can be made of soft polymeric elastomers, for example thermoplastic elastomers (briefly named TPE), ethylene vinyl acetate (briefly named EVA), silicone etc., or other soft and elastic materials. The body connector 410 can be made of hard polymers, for example polycarbonate (briefly named PC), polypropylene (briefly named PP) etc., or other hard materials.

Please refer to FIG. 7A, the tongue protector of the present adjustable oral interface also can be provided with a mechanism for controlling forward and backward movements of the user's lower mandible. For example, an auxiliary axis can be provided at ears 122a, 122b of the tongue protector 120, or at ears 422a, 422b of the tongue protector 420. The axis 113 of the body connector 110 works together with the auxiliary axis, or the axis pin 430 of the body connector 410 works together with the auxiliary axis can change the position of the tongue protector to move the user's lower mandible forward or backward to fit the inclination of the user's lower dental bed.

Please refer to FIG. 7B, the negative pressure deliverable part of the present adjustable oral interface can be pivoted around the axis of the body connector (for example the axis 113 of the body connector 110 or the axis pin 430 of the body connector 410) to adjust its position to fit different oral anatomy of users.

Please refer to FIG. 7C, preferably, the negative pressure deliverable part of the adjustable oral interface may have a longitudinal length mating with a distance between the upper dental and the soft palate portion near the uvula to increase the space and soft tissues inside the oral cavity that the negative pressure can affect.

Please refer to FIG. 7D, preferably, a thickness of a rear end of the negative pressure deliverable part of the adjustable oral interface is larger than a thickness of its front end to increase the soft tissue area inside the oral cavity that the negative pressure can affect, and to increase the negative pressure delivery efficacy and decrease the negative pressure delivery difference as well.

Figure 8B:
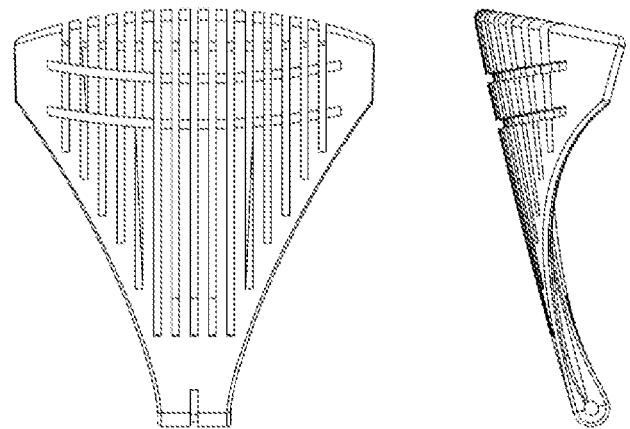
FIG. 8B is schematic views of another variance of a negative pressure deliverable part of an adjustable oral interface of the present invention, in which a width of a rear end of the negative pressure deliverable part is larger than a width of its front end.
Figure 8A:
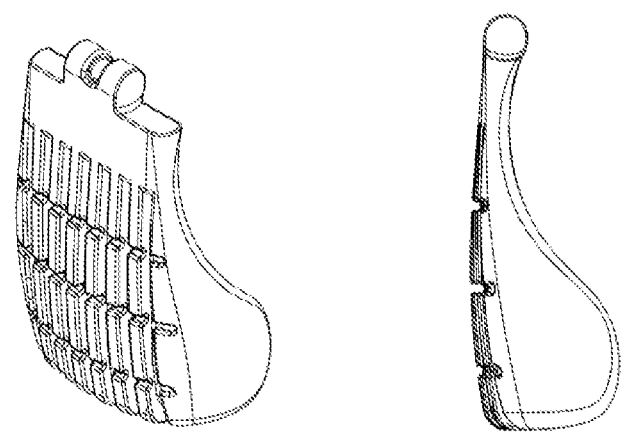
FIG. 8A is schematic views of a variance of a negative pressure deliverable part of an adjustable oral interface of the present invention, in which a thickness of a rear end of the negative pressure deliverable part is larger than a thickness of its front end.
Figure 8:
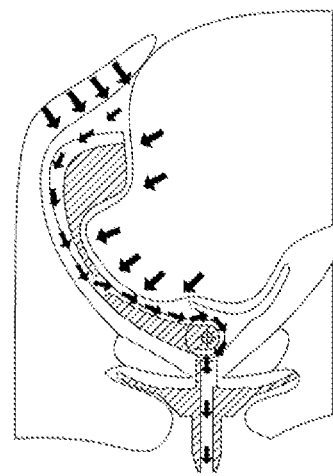
FIG. 8 is a schematic view showing a negative pressure delivery path of a negative pressure deliverable part of an adjustable oral interface of the present invention, in which a thickness of a rear end of the negative pressure deliverable part is larger than a thickness of its front end.

Please refer to FIG. 8, which illustrates air flow directions inside the oral cavity and the movement of the soft palate and tongue when the adjustable oral interface provided with a negative pressure deliverable part having a thin and narrow front end and a thick and wide rear end is in use. The thin and narrow front end of the negative pressure deliverable part is advantageous for providing space to accommodate the tongue. The wide rear end of the negative pressure deliverable part near the hard palate rear portion and the soft palate may increase the soft palate area absorbed by the negative pressure. FIG. 8A and FIG. 8B illustrate the negative pressure deliverable part with the thin and narrow front end and the thick and wide rear end.

Figure 9B:
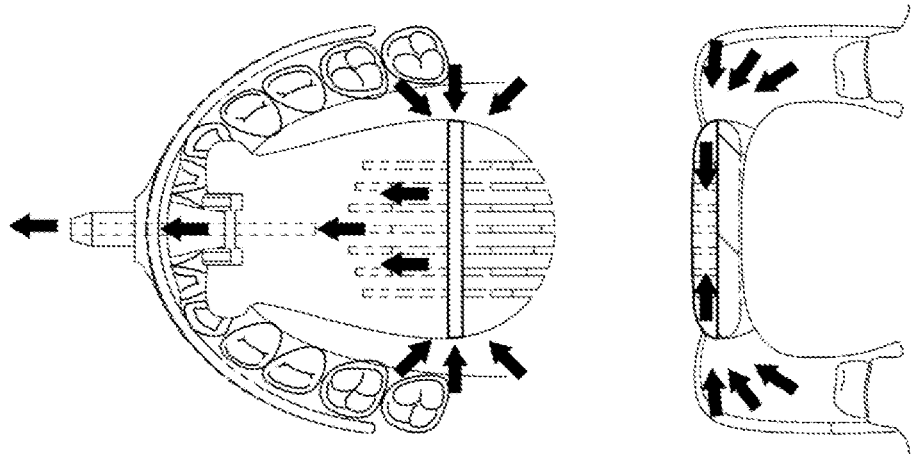
FIG. 9B is schematic views showing another variance of a negative pressure deliverable part of an adjustable oral interface of the present invention, in which the upper drawing shows a top view of the negative pressure deliverable part; and the lower drawing shows a rear view of the negative pressure deliverable part.
Figure 9A:
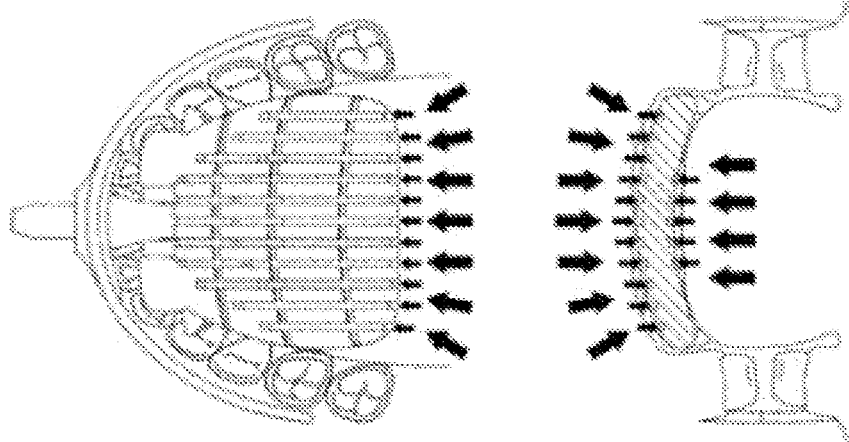
FIG. 9A is schematic views showing a variance of a negative pressure deliverable part of an adjustable oral interface of the present invention, in which the upper drawing shows a top view of the negative pressure deliverable part; and the lower drawing shows a rear view of the negative pressure deliverable part.

Please refer to FIG. 9A and FIG. 9B, which illustrate a phenomenon that a negative pressure delivery path of the longitudinal open fluid channels and traverse open fluid channels of the negative pressure deliverable part of the adjustable oral interface expels liquid inside the user's oral cavity to keep air free flow to insure a desired pressure delivery path. Further, the open fluid channels occupy an area ratio of the negative pressure deliverable part benefits a negative pressure delivery efficacy.

Figure 10F:
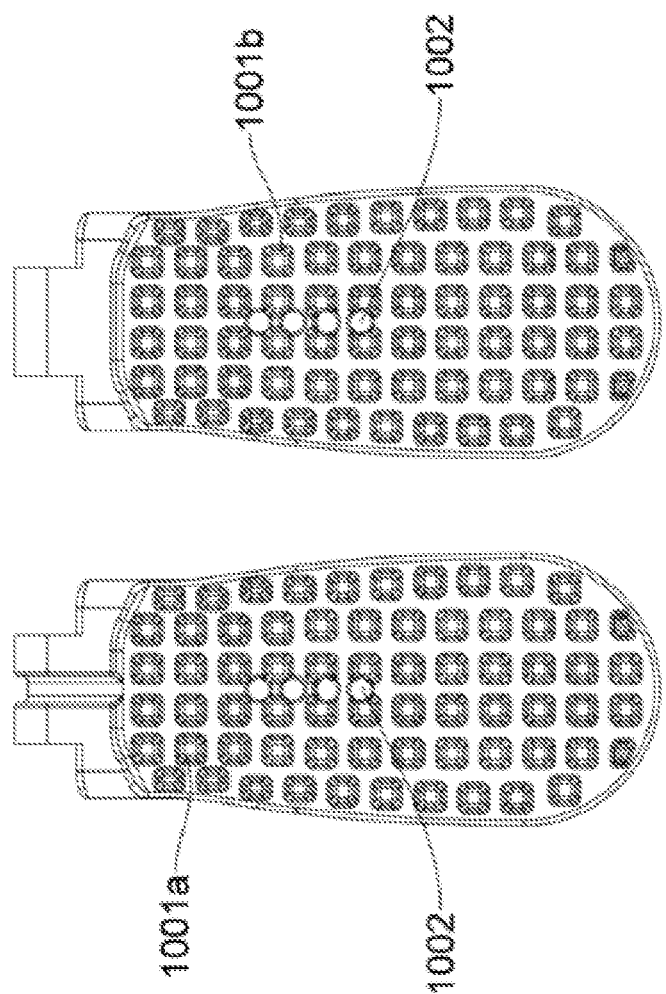

FIG. 10A shows a variance of the negative pressure deliverable part 130 of the first embodiment. FIG. 10B, FIG. 10C, FIG. 10D and FIG. 10E show variances of the negative pressure deliverable part 440 of the second embodiment. Another variance of the negative pressure deliverable part 130 of the first embodiment is shown in FIG. 10F. The negative pressure deliverable part shown in FIG. 10F is provided with a plenty of protrusions 1001a on the top surface thereof to form a plenty of trenches in a substantially mesh-shaped pattern. The bottom surface of the negative pressure deliverable part is provided with a plenty of protrusions 1001b to form a plenty of trenches in a substantially mesh-shaped pattern. As shown in FIG. 10F, the negative pressure deliverable part includes one or more through openings 1002 fluidly communicated between the top surface and the bottom surface of the negative pressure deliverable part. The negative pressure deliverable part of the present adjustable oral interface is configurable by different sizes, different diameters and different shapes to accommodate oral anatomy of different users, and it is detachable and interchangeable and easy to clean and/or be replaced.

Figure 11B:
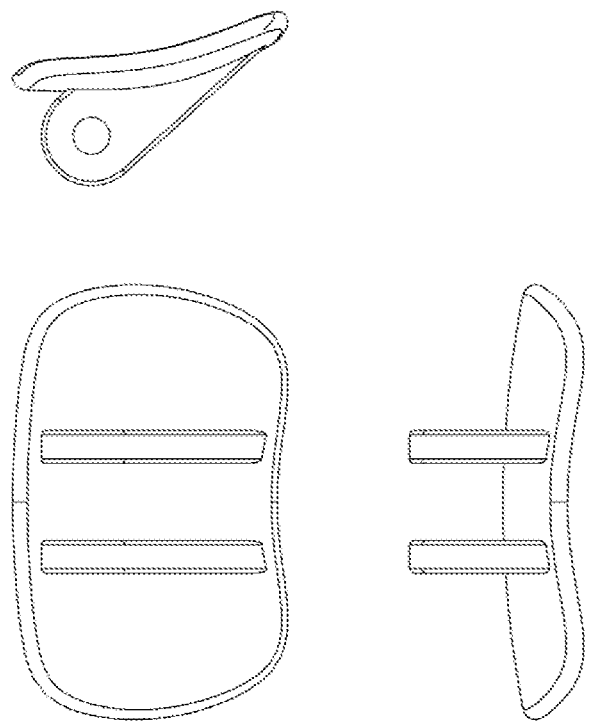
FIG. 11A to FIG. 11E show several variances of a tongue protector of an adjustable oral interface of the present invention.
Figure 11A:
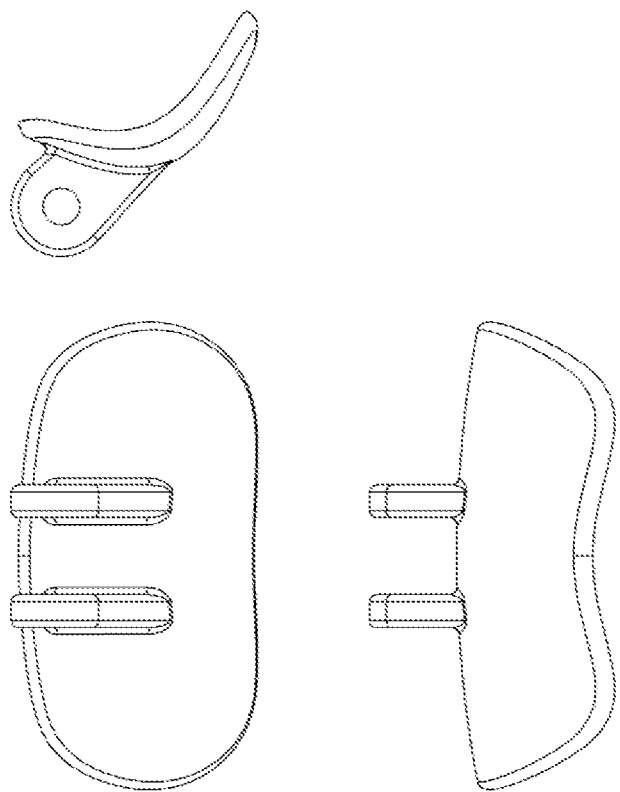
Figure 11D:
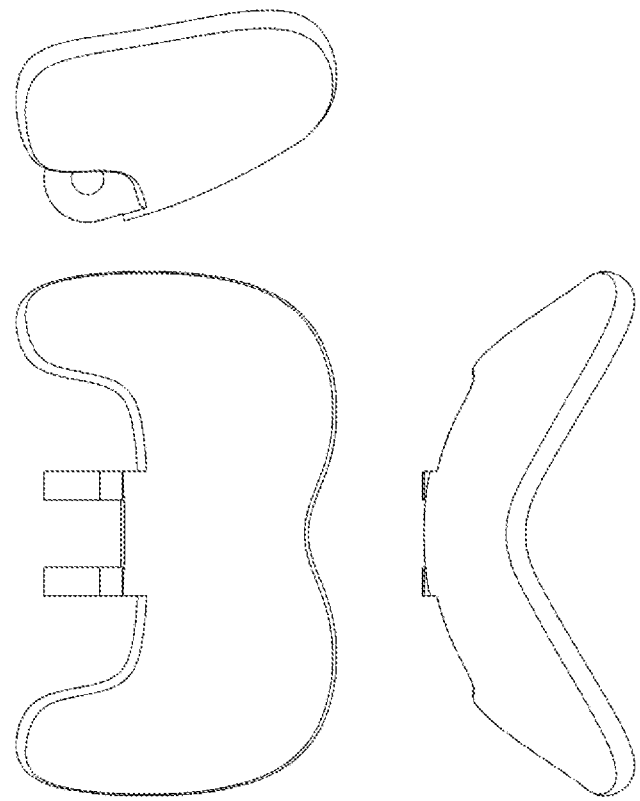
Figure 11C:
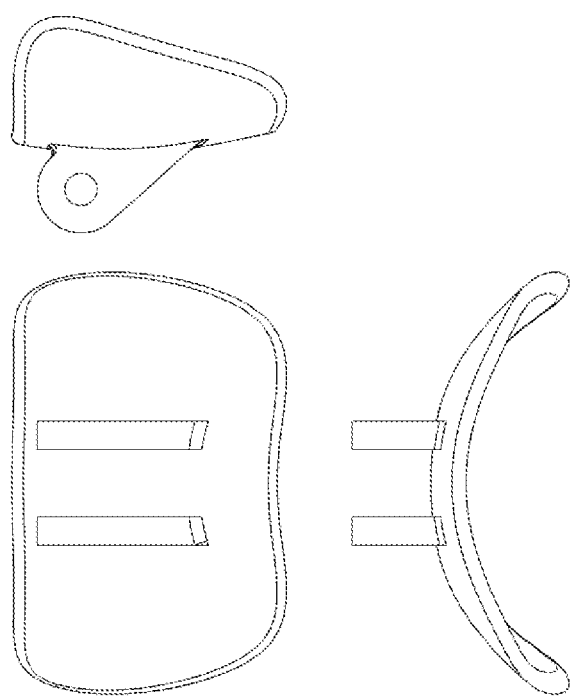
Figure 11E:
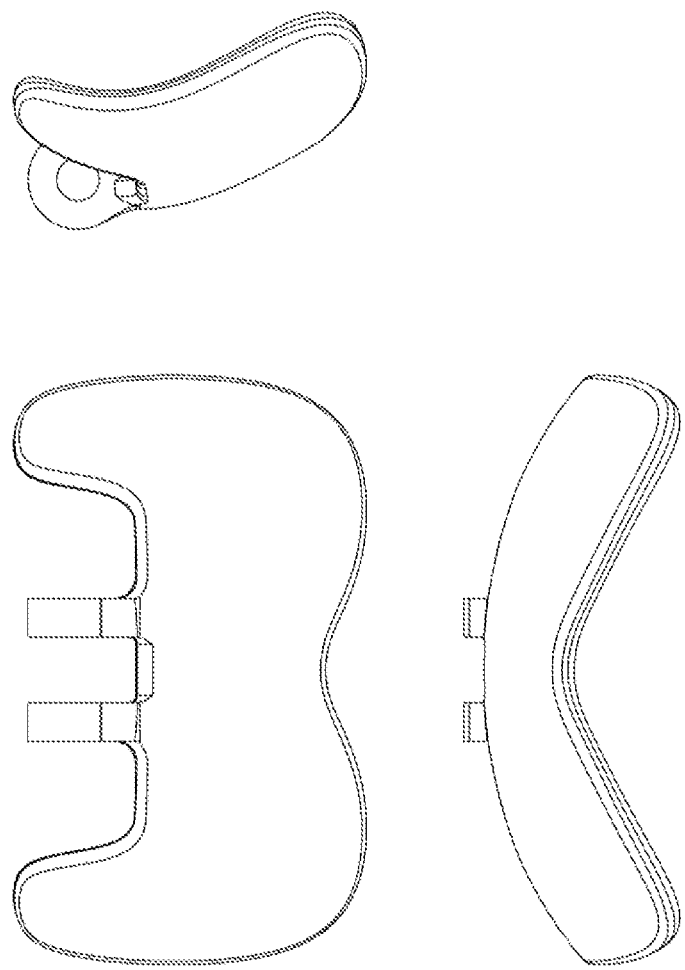

The tongue protector of the present adjustable oral interface is configurable by different sizes and different shapes to accommodate oral anatomy of different users. For example, FIG. 11A, FIG. 11B, FIG. 11C, FIG. 11D and FIG. 11E show some variances of the tongue protector. The tongue protectors shown in FIG. 11A and FIG. 11B are suitable for a user whose tongue tip is sensitive but his/her canine does not stimulate the tongue tip. The tongue protector shown in FIG. 11C is suitable for a user whose upper and lower front teeth are more upright. The tongue protector shown in FIG. 11D is suitable for a user whose lateral sides of the tongue tip are sensitive but his/her front teeth have less curvatures.

Figures 12A, 12B:
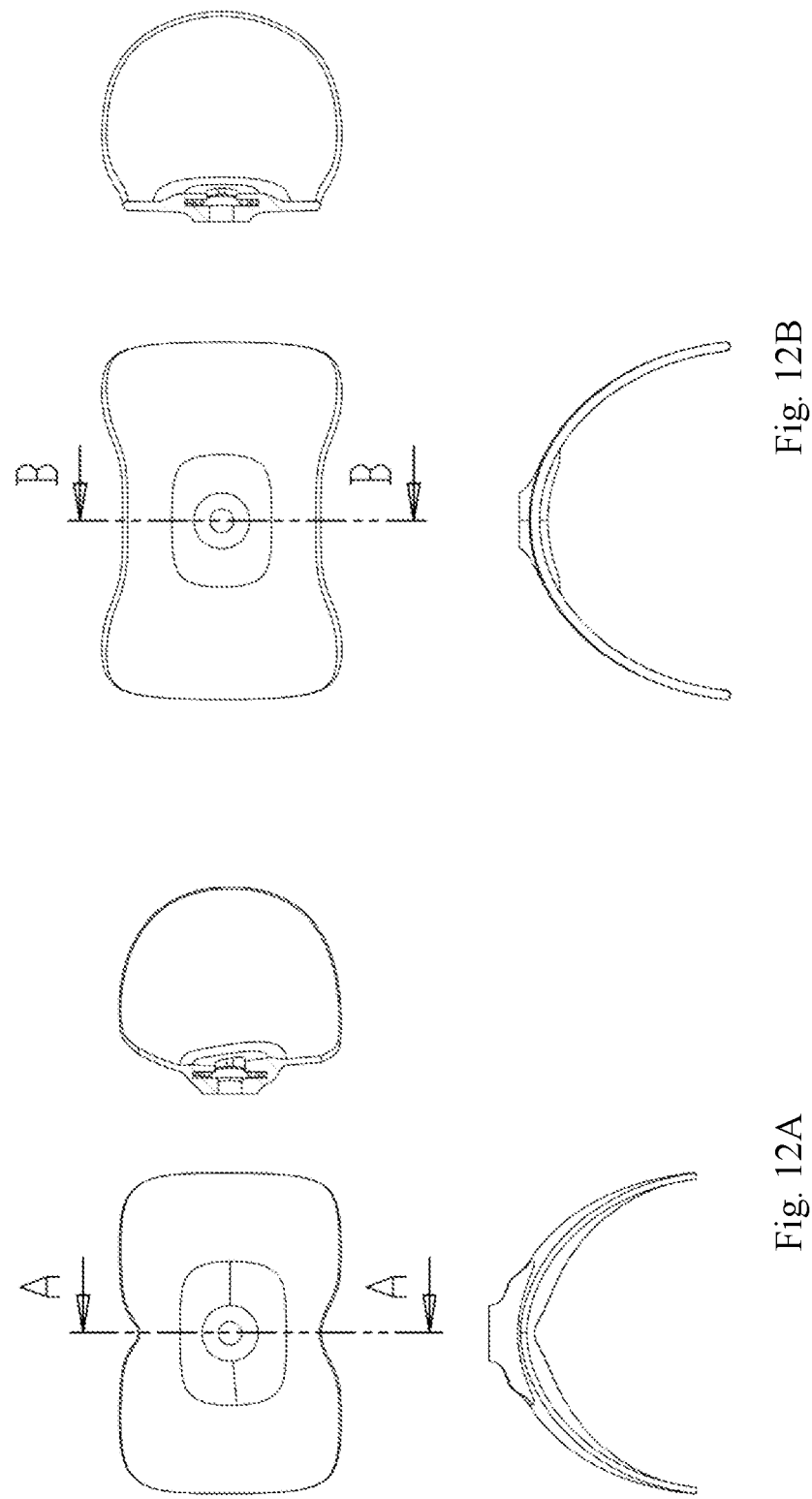

The shield of the present adjustable oral interface is configurable by different sizes and different shapes to accommodate oral anatomy of different users, for example, variances as shown in FIG. 12A, FIG. 12B and FIG. 12C. The shield of FIG. 12A is suitable for a user with upper front teeth more forward than lower front teeth. The shield of FIG. 12B is suitable for a user with more upright front teeth. The shield of FIG. 12C is suitable for a user with upper and lower front teeth having more inclination.

Figures 13A, 13B:
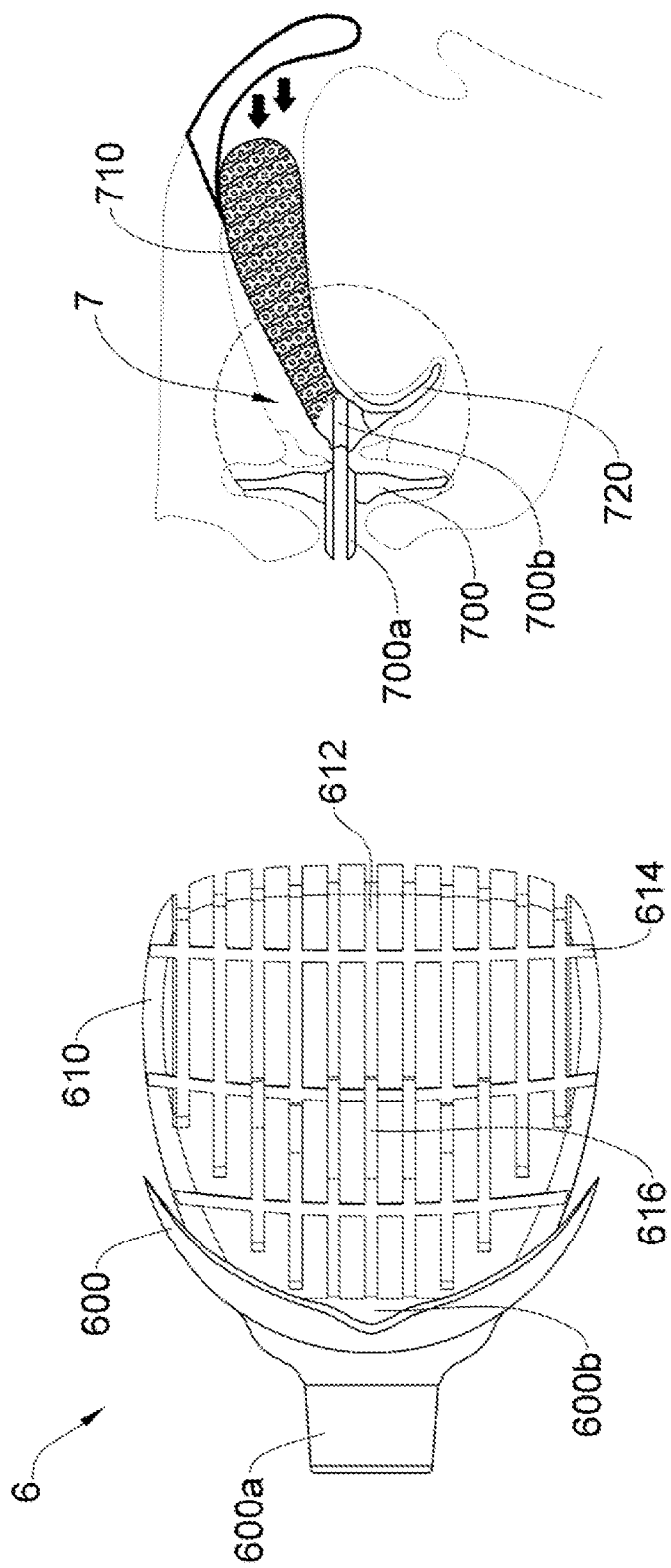
FIG. 13A is a schematic top view of an adjustable oral interface according to a third embodiment of the present invention.
FIG. 13B is a schematic cross-sectional side view of an adjustable oral interface according to a fourth embodiment of the present invention.

FIG. 13A shows a schematic top view of an adjustable oral interface 6 of the present negative pressure therapy system according to a third embodiment of the present invention. The adjustable oral interface 6 includes a shield 600, a negative pressure deliverable part 610 and a tongue protector (not shown in FIG. 13A). When the adjustable oral interface 6 is worn in the oral cavity of a user, the shield 600 is situated between lips and front teeth of the user. The shield 600 can be made of thermoplastic materials which can be remolded through compression on the front teeth and formed a configuration which fits the anatomy features of the user. The shield 600 also functions as a seal to prevent the user's oral cavity from air leakage. The shield 600 has a front extension fluid channel 600a protruding out of the user oral cavity and connecting to a fluid conduit (not shown in the drawing). The shield 600 has a rear end 600b in a form of an open fluid channel. The negative pressure delivery part 610 can be made of thermoplastic material with remolding property to benefit it can be remolded through compression and formed a configuration which fits the contour of the space between the tongue and upper palate of the user. The body of the negative pressure deliverable part 610 has a similar structure as the body 132 of the negative pressure deliverable part 130 of the first embodiment. That is, the negative pressure deliverable part 610 includes longitudinal open fluid channels 612, traverse open fluid channel 614 and through openings 616 passing through its top and bottom surfaces. The longitudinal open fluid channels 612 fluidly communicates with the rear end 600b of the shield 600. The tongue protector is combined with the shield 600 and positioned beneath the negative pressure deliverable part 610.

FIG. 13B shows a schematic cross-sectional view of an adjustable oral interface 7 of the present negative pressure therapy system according to a fourth embodiment of the present invention. The adjustable oral interface 7 includes a shield 700, a negative pressure deliverable part 710 and a tongue protector 720. When the adjustable oral interface 7 is worn in the oral cavity of a user, the shield 700 is situated between lips and front teeth of a user. The shield 700 can be made of thermoplastic material which can be remolded through compression on the front teeth and formed a configuration which fits the anatomy features of the user. The shield 700 also functions as a seal to prevent the user's oral cavity from air leakage. The shield 700 has a front extension fluid channel 700a protruding out of the user oral cavity and connecting to a fluid conduit (not shown in the drawing). The shield 700 has a rear end 700b in a form of a fluid channel fluidly communicated with the front extension fluid channel 700a. The negative pressure deliverable part 710 can be made of porous material to benefit fluid flows through top and lower surfaces of the negative pressure deliverable part 710 to deliver negative pressure. The front of the negative pressure deliverable part 710 is fluidly communicately combined with a rear end 700b of the shield 700. The rear end of the negative pressure deliverable part 710 is near the soft palate of the user. The tongue protector 720 is combined with the rear end 700b of the shield 700 and positioned beneath the negative pressure deliverable part 710.

In an implementation, a longitudinal length of the present negative pressure deliverable part, for example, is 5 mm-80 mm, particularly 10 mm-70 mm, and more particularly 15 mm-60 mm, but it is not limited to these length dimensions.

In some implementations, the open fluid channels of the present negative pressure deliverable part occupy an area ratio of 0%-100% of the negative pressure deliverable part, particularly 5%-95%, and more particularly 10%-90%. When the open fluid channels occupy an area ratio of 0% of the negative pressure deliverable part, it means the negative pressure deliverable part does not have any fluid channel, or the fluid channel occupies a very small area of the negative pressure deliverable part. Under this circumstance, the negative pressure deliverable part is realized by the negative pressure deliverable part 710 of FIG. 13B. When the open fluid channel occupies an area ratio of 100% of the negative pressure deliverable part, it means the open fluid channel occupies a huge area of the negative pressure deliverable part, and the negative pressure deliverable part can be realized by a U-shaped tank body (not shown in the drawing). Specifically, for example, the U-shaped tank body may have two opposite lateral thin walls along a longitudinal dimension of the negative pressure deliverable part, and one end of the U-shaped tank body combined with the shield is far away from the back of the tongue. An artisan in the field can practice the afore-described configuration of the negative pressure deliverable part according to above disclosure of the present invention.

The foregoing description is only embodiments of the present invention, not used to limit the scope and range of the present invention. Those equivalent changes or modifications made according to the shape, structure, feature, or spirit described in the claims of the present invention are included in the appended claims of the present invention.

What is claimed is:

1. An adjustable oral interface for a negative-pressure therapy system, comprising:
   a shield adapted for being situated between a user's lips and front teeth;
   a negative pressure deliverable part coupled with the shield; wherein the negative pressure deliverable part has a front end in proximity to the user's tongue tip and a rear end in proximity to the user's soft palate;
   a tube fluidly communicated between the negative pressure deliverable part and a negative pressure generation source;
   a body connector coupled to the shield and fluidly communicated between the negative pressure deliverable part and the tube, wherein the body connector is provided with an axis being adapted for being close to the user's tongue tip to pivotally assemble the negative pressure deliverable part to the body connector; and
   a tongue protector being individually pivotally assembled to the axis of the body connector to change and adjust its position in relative to the axis so as to be adapted for fitting an oral anatomy of the user,
   wherein the body connector excludes a bite structure, and the body connector has a length from a left side to a right side of the body connector smaller than a length of the tongue protector from a left side to a right side of the tongue protector, and the length of the tongue protector is smaller than a length of the shield from a left side to a right side of the shield, and
   wherein the shield, the tongue protector and the negative pressure deliverable part are individually detachable and interchangeable from the adjustable oral interface, the negative pressure deliverable part is adapted for being adjustable to be situated at a space between the user's tongue and upper palate so as to be conformable to the contour of the upper palate, whereby the adjustable oral interface delivers negative pressure via the negative pressure deliverable part to a front and back of the user's oral cavity to eliminate air space between the tongue and the upper palate, and the tongue protector is adapted for being situated beneath the user's tongue in proximity to the user's tongue tip.

2. The adjustable oral interface as claimed in claim 1, wherein the shield is configurable by different sizes and/or different shapes.

3. The adjustable oral interface as claimed in claim 2, wherein the shield is a thin piece.

4. The adjustable oral interface as claimed in claim 3, wherein the shield is shaped to fit a space between an inner surface of the user's lips and an outer surface of the front teeth.

5. The adjustable oral interface as claimed in claim 1, wherein the negative pressure deliverable part has one or more of open fluid channels.

6. The adjustable oral interface as claimed in claim 5, wherein the one or more of open fluid channels occupies an area ratio of the negative pressure deliverable part that benefits a negative pressure delivery efficacy.

7. The adjustable oral interface as claimed in claim 6, wherein the one or more of open fluid channels occupies an area ratio of 0~100% of the negative pressure deliverable part.

8. The adjustable oral interface as claimed in claim 2, wherein the shield has a length of 10 mm to 120 mm from a left side to a right side of the shield.

9. The adjustable oral interface as claimed in claim 5, wherein the negative pressure deliverable part has the more open fluid channels configured in an isometric pattern.

10. The adjustable oral interface as claimed in claim 5, wherein the one or more of open fluid channels are configured in parallel with a longitudinal axis of the negative pressure deliverable part.

11. The adjustable oral interface as claimed in claim 5, wherein the one or more open fluid channels is perpendicular to a longitudinal axis of the negative pressure deliverable part.

12. The adjustable oral interface as claimed in claim 1, wherein the shield functions as a seal.

13. The adjustable oral interface as claimed in claim 1, wherein the negative pressure deliverable part is made of the thermoplastic elastomers.

14. The adjustable oral interface as claimed in claim 1, wherein the shield is made of thermoplastic elastomers.

15. The adjustable oral interface as claimed in claim 1, wherein the negative pressure deliverable part is made of elastic porous materials.

16. The adjustable oral interface as claimed in claim 1, wherein the negative pressure deliverable part comprises a through hole fluidly communicated upper and lower surfaces of the negative pressure deliverable part.

17. The adjustable oral interface as claimed in claim 1, wherein the negative pressure deliverable part is configurable by different sizes, different diameters, and different shapes.

18. The adjustable oral interface as claimed in claim 1, wherein a thickness of the rear end of the negative pressure deliverable part is larger than a thickness of the front end of the negative pressure deliverable part, and a width of the rear end is larger than a width of the front end.

19. The adjustable oral interface as claimed in claim 1, wherein the tongue protector is configurable by different sizes, different diameters, and different shapes.

20. The adjustable oral interface as claimed in claim 1, wherein the tongue protector further comprises an auxiliary axis to work together with the axis of the body connector to control forward and backward movements of the user's lower mandible.

21. The adjustable oral interface as claimed in claim 1, wherein the body connector is made of hard materials.

\* \* \* \* \*